(12) United States Patent
Garibaldi et al.

(10) Patent No.: US 6,401,723 B1
(45) Date of Patent: Jun. 11, 2002

(54) MAGNETIC MEDICAL DEVICES WITH CHANGEABLE MAGNETIC MOMENTS AND METHOD OF NAVIGATING MAGNETIC MEDICAL DEVICES WITH CHANGEABLE MAGNETIC MOMENTS

(75) Inventors: Jeffrey M. Garibaldi, St. Louis, MO (US); Roger N. Hastings, Maple Grove, MN (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/504,835

(22) Filed: Feb. 16, 2000

(51) Int. Cl.⁷ ............................................. A61B 19/00
(52) U.S. Cl. .................................................. 128/899
(58) Field of Search .................. 600/585, 12; 128/899; 604/276, 95; 606/108, 130

(56) References Cited

U.S. PATENT DOCUMENTS

| | | | |
|---|---|---|---|
| 5,353,807 A | * 10/1994 | DeMarco | 600/585 |
| 5,845,646 A | 12/1998 | Lemelson | |
| 6,015,414 A | * 1/2000 | Werp et al. | 606/108 |
| 6,058,323 A | 5/2000 | Lemelson | |
| 6,216,026 B1 | 4/2001 | Kuhn et al. | |
| 6,233,474 B1 | 5/2001 | Lemelson | |

* cited by examiner

*Primary Examiner*—Kevin Shaver
*Assistant Examiner*—Brian Szmal
(74) *Attorney, Agent, or Firm*—Harness, Dickey & Pierce, P.L.C.

(57) ABSTRACT

A method of navigating a medical device having a changeable magnetic moment within an operating region within a patient, the method includes applying a navigating magnetic field to the operating region with an external source magnet, and changing the direction of the magnetic moment in the medical device to change the orientation of the medical device in a selected direction within the operating region. The magnet moment of the medical device can be created by one or more electromagnet coils, in which case the magnetic moment can be changed by changing the current to the coil. Alternatively, the magnetic moment of the medical device can be created by one or more permanent magnets, in which case the magnetic moment can be changed by mechanically or magnetically manipulating the permanent magnet.

35 Claims, 4 Drawing Sheets

MAGNETIC MEDICAL DEVICES WITH CHANGEABLE MAGNETIC MOMENTS AND METHOD OF NAVIGATING MAGNETIC MEDICAL DEVICES WITH CHANGEABLE MAGNETIC MOMENTS

BACKGROUND OF THE INVENTION

This invention relates to the magnetic navigation of medical devices, and in particular to magnetic medical devices with changeable magnetic moments, and to methods of navigating magnetic medical devices with changeable magnetic moments.

It has long been proposed to magnetically navigate catheters through the body with an externally applied magnetic field. Recent advances have made the magnetic navigation of catheters and other medical devices practical. Typically, the medical device is provided with a permanent or a permeable magnetic element. An external source magnet, which may be a permanent magnet, an electromagnet, or a superconducting electromagnet, is used to apply a magnetic field and/or gradient to an operating region inside a patient to act on the magnetic element in the medical device to orient and/or move the medical device in the operating region. The medical device is oriented and/or moved by changing the magnetic field and/or gradient applied by the external source magnet.

In the case of stationary electromagnetic and superconducting electromagnetic source magnets, changing the magnetic field and/or gradient is accomplished by changing the currents supplied to the source magnet. In the case of moveable source magnets, changing the magnetic field and/or gradient is accomplished by changing the position and/or orientation of the source magnet. If the moveable source magnet is an electromagnet or a superconducting electromagnet, the magnetic field and/or gradient can also be changed by changing the current supplied to the magnet.

While systems with stationary electromagnets and superconducting electromagnets provide fast, safe, and effective navigation of medical devices, it can be expensive to construct and maintain a system that operates in real time to provide unrestricted navigation in the body. Similarly while systems with moving source magnets provide fast, safe, and effective navigation of medical devices, it can be expensive to construct and maintain a system that can accurately move the source magnets to make a selected change in the magnet field and/or gradient.

The changing fields and gradients created by the source magnets are strong and will usually require shielding at many health care facilities. This shielding is another difficulty and expense of magnetic navigation systems that employ changing source magnetic fields and gradients to navigate magnetic medical devices in the body.

While systems using changing source magnet magnetic fields and gradients provide precise control and a high degree of navigational flexibility, for some types of medical procedures a less complicated, less expensive, and preferably more compact navigation system would be desirable.

SUMMARY OF THE INVENTION

Generally according to the principles of the present invention a magnetic medical device having a changeable magnetic moment is introduced into an operating region in the body, a navigating magnetic field is applied to the operating region, and the magnetic moment of the magnetic medical device is changed to orient the magnetic medical device relative to the externally applied navigating magnetic field.

As used herein a magnetic medical device having a changeable magnetic moment does not include magnetic medical devices that have a permeable magnetic material in which a magnetic moment is induced in the permeable magnetic material by the application of the navigating magnetic field, but only to magnetic medical devices in which the change in the magnetic moment direction is independent from the navigating magnetic field, and the magnetic moment is acted upon by the navigating magnetic field.

According to the first embodiment of the invention, the magnetic medical device includes at least one electromagnetic coil, and preferable more than one coil, so that the magnetic moment of the medical device can be changed by changing the current in the at least one electromagnetic coil. This causes the magnetic medical device to move with respect to the externally applied navigating magnetic field.

According to a second embodiment, the magnetic medical device includes a moveable permanent magnet, movement of which causes the magnetic moment of the medical device to change. In a first construction or this second embodiment, the permanent magnet is moved with a mechanism. In a second construction of this second embodiment, the permanent magnet is moved with one or more electromagnetic coils that selectively create a local magnetic field to orient the permanent magnet to change the magnetic moment of the magnetic medical device. A lock can be provided to selectively lock the permanent magnet in its selected position.

According to a third embodiment, the magnetic medical device includes a moveable permanent magnet, movement of which causes the magnetic moment of the medical device to change. The permanent magnet is lockable in the magnetic medical device, so that its orientation remains fixed relative to the magnetic medical device. The orientation of the permanent magnet relative to the magnetic medical device can be changed by unlocking the permanent magnet, applying an external configuring magnetic field to change the orientation of the permanent magnet, and locking the permanent magnet. The external configuring magnetic field can then be removed, and an external navigating magnet field applied to orient the magnetic medical device with its new magnetic moment.

BRIEF DESCRIPTION OF THE DRAWINGS

Corresponding reference numbers indicate corresponding parts throughout the drawings.

DETAILED DESCRIPTION OF THE INVENTION

Figure 1:
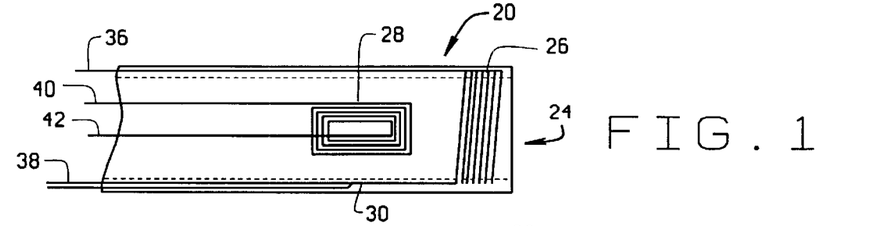
FIG. 1 is a top plan view of the distal end of a magnetic medical device constructed according to a first embodiment of this invention.
Figure 2:
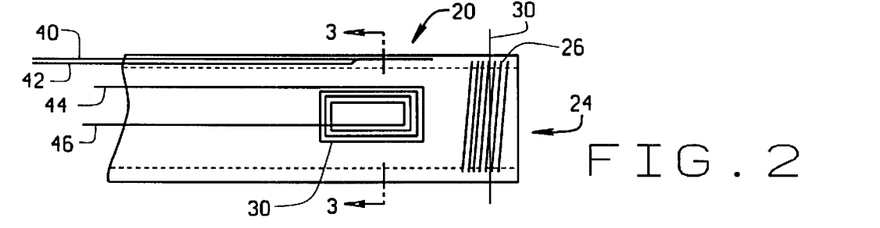
FIG. 2 is a side elevation view of the distal end of the magnetic medical device of the first embodiment.
Figure 3:
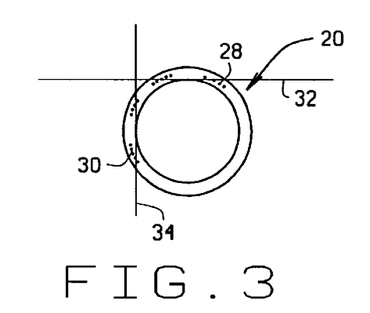
FIG. 3 is a transverse cross-sectional view of the magnetic medical device taken along the plane of line 3—3 in FIG. 2.

A first embodiment of a magnetic medical device constructed according to the principles of this invention is indicated generally as 20 in FIGS. 1–7. While as shown in FIGS. 1–3 the magnetic medical device 20 is a catheter having a sidewall defining a lumen therein, this invention is not so limited and the magnetic medical device 20 could be any other medical device that a physician might want to navigate in the body, such as an electrode, a biopsy tool, or an endoscope.

The magnetic medical device 20 is preferably an elongate medical device having a proximal end (not shown) and a distal end 24 that is inserted into and navigated inside the patient's body. The magnetic medical device 20 is preferably sufficiently flexible to allow the distal end portion to flex under the forces generated by external magnetic field acting on the magnetic moment of the magnetic medical device to permit navigation of the device through the body. According to the principles of this invention, there is at least one coil adjacent the distal end 24 of the magnetic medical device 20 which can be selectively energized to change the magnetic moment near the distal end 24 of the magnetic medical device 20. In the preferred embodiment there are three coils 26, 28, and 30, which are preferably arranged in three mutually perpendicular planes. The coil 26 is preferably embedded in the wall of the magnetic medical device 20 adjacent the distal end 24 and extends circumferentially around the distal end portion of the magnetic medical device 20. The coil 26 is generally oriented in a plane 30 transverse to the axis of the magnetic medical device 20. The coil 28 is also preferably embedded in the wall of the magnetic medical device 20 near the distal end 24. The coil 28 is generally in a plane 32 parallel to the longitudinal axis of the magnetic medical device 20. The coil 30 is likewise preferably embedded in the wall of the device. The coil 30 is generally in a plane 34 parallel to the longitudinal axis of the device and perpendicular to the plane 32 in which coil 28 lies.

Leads 36 and 38 extend to coil 26, leads 40 and 42 extend to coil 28, and lead longitudinal 44 and 46 extend to coil 30. The leads 36, 38, 40, 42, 44 and 46 allow current to be supplied to coils 26, 28 and 30 to create a magnetic moment of a selected direction and intensity. While the coils 26, 28, and 30 are shown arranged in mutually perpendicular planes, they could be arranged in some other configuration provided that the coils provide sufficiently broad selection of magnetic moment directions for reasonable navigation. Of course, the coils 26, 28, and 30 could be provided with either or both a common power supply lead and a common ground lead, to reduce the number of lead extending from the distal end of the magnetic medical device to the proximal end of the device, and to simplify construction.

The magnetic torque on the distal end of the catheter is directly proportional to the magnetic moment of the magnetic medical device and to the applied navigating magnetic field. For a coil, the magnetic moment is directly proportional to the product of the number of turns in the coil, the current through the coil, and the cross-sectional area of the coil wire. For example, for a typical catheter with diameter of 2 mm, the coil 26 may be wound with 1,000 turns of AWG #50 magnet wire having a diameter of 0.025 mm. This corresponds to a 5 mm long coil with 5 layers having total thickness of 0.125 mm imbedded into the catheter wall. When 0.1 amps of current are applied through this coil, the coil creates a magnetic moment of 0.4 nano-Tesla-cubic meter. For comparison, a neodymium-boron-iron magnet of a comparable size (5 mm long, 2 mm diameter, and 0.125 mm thick) has a magnetic moment of about 4 nano-Tesla-cubic meter. Thus a coil for creating a variable magnetic moment should be operated in an externally applied navigating magnetic field about ten times that required for a similar sized permanent magnet to achieve the same magnetic torque at the catheter tip.

Currents of 0.1 amps and larger applied continuously through the coils will typically cause the coil temperature to rise. In many applications the coil is naturally cooled, such as by convention to flowing blood in vascular navigation, or by conduction to a static liquid pool of body fluid. However, as discussed below, in some applications it may be desirable to cool the coils by supplying a continuous flow of a coolant within the catheter. It may be desirable to provide thermally insulating material between the coil and the outside surface of the catheter which contacts body tissues. Alternatively, or additionally, heat can be conducted away from the distal end 24 of the catheter 20 and distributed throughout a larger volume of the catheter by providing electrical lead wires that are build up of multiple strands to create a flexible yet massive thermally conducting conduit, as discussed in more detail below.

Each of the coils 28 and 32 are constructed from 150 turns of AWG #50 magnet wire. The coils are 10 mm long with 5 layers imbedded in the wall of the magnetic medical device 20. The total magnetic moment of the two coils is 0.4 nano-Tesla-cubic meter, the same as the longitudinal coil 26.

Figure 4:
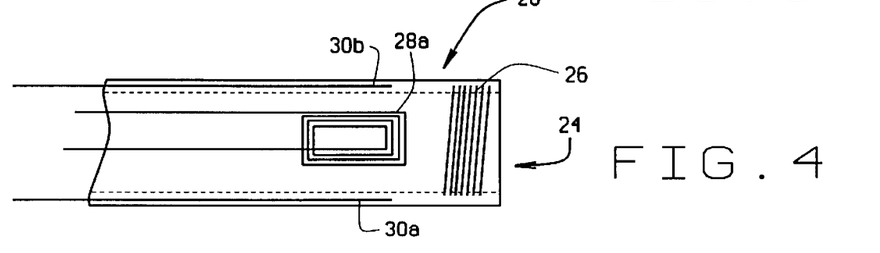
FIG. 4 is a top plan view of the distal end of a first alternate construction of the magnetic medical device of the first embodiment, in which the coils comprise multiple coil sections arranged in series.
Figure 5:
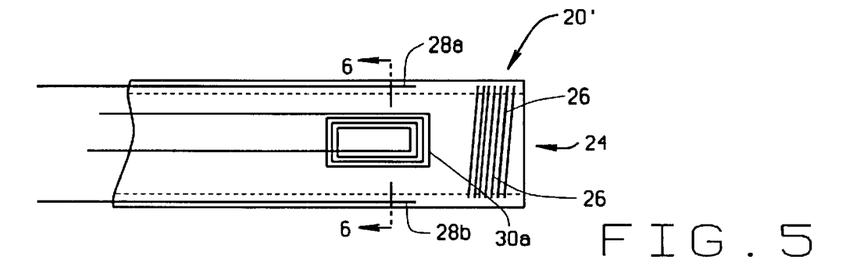
FIG. 5 is a side elevation view of the distal end of the magnetic medical device of the first alternate construction of the first embodiment.
Figure 6:
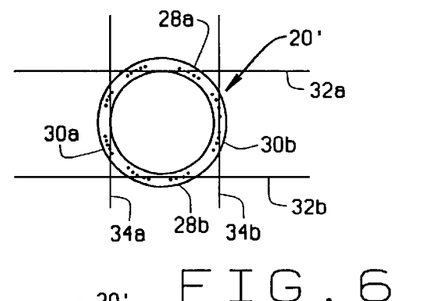
FIG. 6 is a transverse cross-sectional view of the magnetic medical device taken along the plane of line 6—6 in FIG. 5.

As shown in FIGS. 4–6, in a first alternate construction of the magnetic medical device of the first embodiment, indicated generally as 20'. The magnetic medical device 20' is similar in construction to magnetic medical device 20, except that instead of coil 28, device 20' has two sub-coils 28a and 28b, connected in series and arranged on opposite sides of the magnetic medical device, and that instead of coil 30, device 20' has two sub-coils 30a and 30b, connected in series and arranged on opposite sides of the magnetic medical device. As shown in FIG. 6, the sub-coils 28a and 28b are arranged in two generally parallel planes 32a and 32b, and the sub-coils 30a and 30b are arranged in two generally parallel planes 34a and 34b. The planes 32a and 32b are generally perpendicular to the planes 34a and 34b.

As noted above, the coils 26, 28, and 30 tend to heat up in use. At temperatures above about 45°, the coils can be harmful to the surrounding tissue, and at temperatures above about 50°, the coils can kill surrounding tissue. In some applications, for example navigation through the vasculature, the flow of body fluids will sufficiently cool the coils. In other applications, the coils may need to be actively cooled to prevent harmful heating. A second alternate construction of a magnetic medical of the first embodiment is indicated generally as 20" in FIG. 7. The magnetic medical device 20" is similar in construction to magnetic medical device 20, except as shown in FIG. 7 the magnetic medical device 20" includes a reservoir 50 for storing cooling fluid, a pump 52 for circulating cooling fluid, and a tube 54 for delivering cooling fluid to the distal end of the magnetic medical device to cool the coils.

Cooling fluid is pumped by pump 52 from reservoir 50 through tube 54 to the distal end of the magnetic medical device 20". The cooling fluid returns to the reservoir 50 in the annulus between the tube 54 and the internal walls of the magnetic medical device 20". If necessary, the reservoir can be cooled to cool the cooling fluid.

Figures 7, 8:
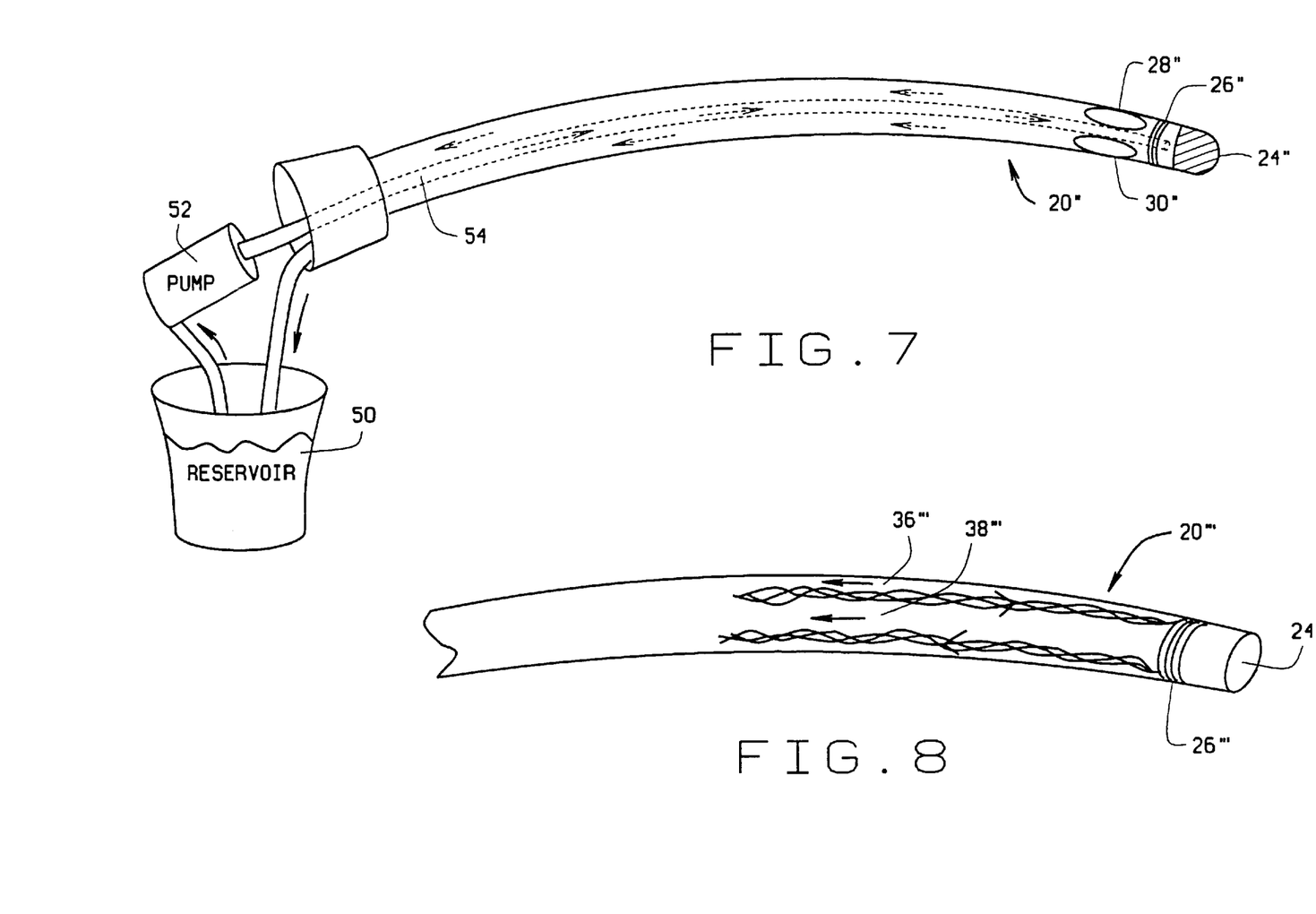
FIG. 7 is schematic diagram of a second alternate construction of the magnetic medical device of the first embodiment, configured for circulation of cooling fluid to prevent the coils from overheating.
FIG. 8 is a schematic diagram of third alternate construction of the magnetic medical device of the first embodiment, with flexible multistranded leads for conducting heat from the coils to prevent the coils from overheating.

A third alternate construction of a magnetic medical device of the first embodiment is indicated generally as 20'" in FIG. 8. The magnetic medical device 20'" is similar in construction to magnetic medical device 20, except as shown in FIG. 8 the magnetic medical device 20'" has flexible multistranded leads for the coils to conduct heat proximally away from the coils. (Only coil 26 is shown in the schematic view of FIG. 5, with leads 36'" and 38'").

Particularly where the coils are not embedded in the walls of the magnetic medical device, they may be covered with a thermally insulating polymer coating to protect tissue that might come into contact with the distal end of the magnetic medical device.

Figures 9, 11:
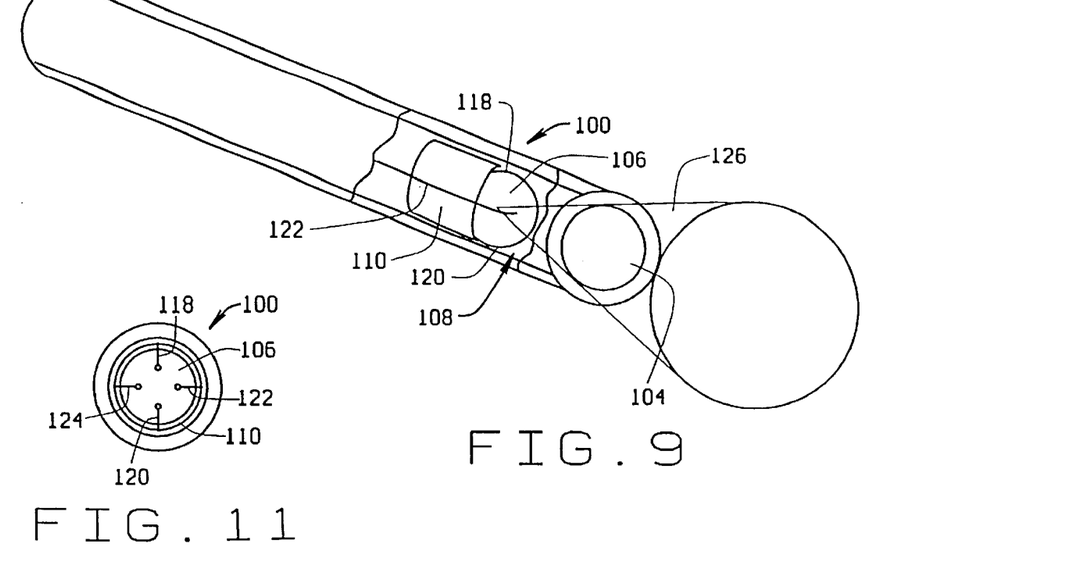
FIG. 9 is a perspective view of the distal end of a magnetic medical device constructed according to a second embodiment of this invention.
FIG. 11 is a transverse cross-sectional view taken along the plane of line 11—11 in FIG. 10A.
Figure 10A:
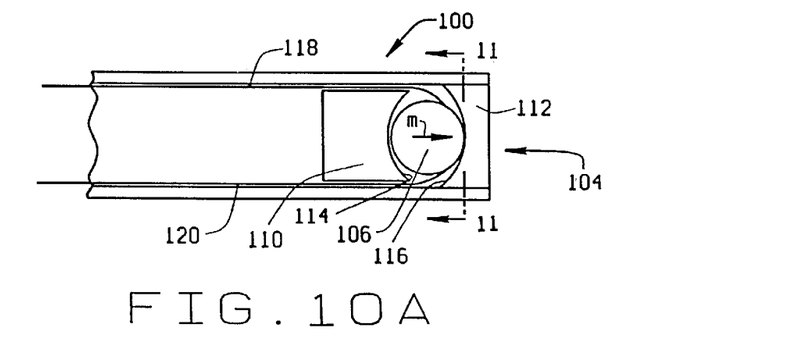
FIG. 10A is a longitudinal cross-sectional view of the distal end of a magnetic medical device of the second embodiment of this invention, showing the permanent magnet in a first orientation.
Figure 10B:
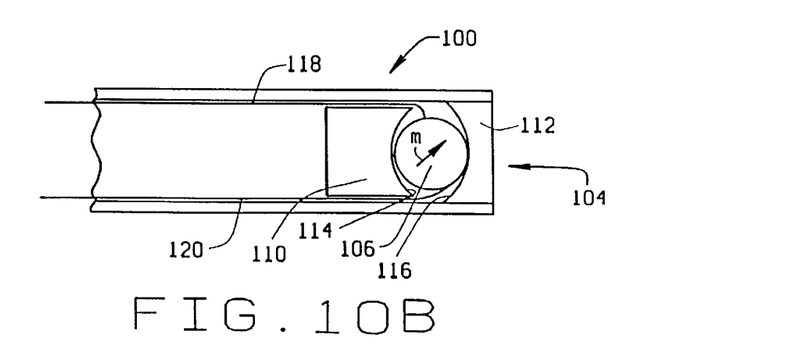
FIG. 10B is a longitudinal cross-sectional view of the distal end of the magnetic medical device of the second embodiment showing the permanent magnet in a second position.

A second embodiment of a magnetic medical device constructed according to the principles of this invention is indicated generally as 100 in FIGS. 9, 10, and 11. As indicated above, the magnetic medical device 100 may be any device that a physician might want to navigate through the body, such as a catheter, an electrode, a biopsy tool, or an endoscope. The magnetic medical device 100 typically has a proximal end (not shown) and a distal end 104. There is a magnet body 106 inside the distal end portion of the magnetic medical device 100. The magnet body 106 is preferably made from a strong permanent magnetic material, such as neodymium-iron-boron, or other suitable material. The magnet body 106 is trapped within a cage 108 formed by supports 110 proximal to the magnet body, and 112 distal to the magnet body. The cage 108 allows the magnet body 106 to rotate, but substantially restricts axial or radial movements. The distal face 114 of the support 110 is smoothly, concavely curved and the proximal face 116 of the support 112 is likewise smoothly, concavely curved to restrict the axial and radial movement of the magnet body 106, while otherwise permitting the magnet body to turn. The magnet body 106 preferably has a smoothly, convexly curved surface to facilitate the movement of the magnet body on the faces 114 and 116. As shown in the figures the magnet body 106 is a sphere, but it could be some other shape, such as an elipsoid.

Two pairs of opposing actuator wires 118, 120 and 122, 124 are attached to the magnet body 106, and extend to the proximal end of the magnetic medical device 100, where they can be operated by pushing and/or pulling. Pulling one actuator wire and/or pushing the other actuator wire in the pair causes the magnet body 106 to turn. The pairs of opposing actuator wires 118, 120 and 122, 124 are preferably located in perpendicular planes, and thus by operating the opposing actuator wires, the direction of the magnetic moment of the can sweep a fairly large range of orientations, as indicated by the 126 cone of the projected magnetic moment shown in FIG. 9. Ideally the magnet will be capable of pointing to all directions in space. Thus, as shown in FIGS. 11A and 11B, the magnetic moment of the magnetic body 106, indicated by arrow m, can be moved by operating the actuator wires 118, 120.

Of course, instead of actuator wires 118, 120 and 122, 124, some other mechanism could be used to selectively reorient the magnet body 106. The mechanism can be any other mechanism that can reorient the magnet body can be used, and this mechanism preferably allows the magnet body 106 to be oriented so that the magnet moment can be moved to any selected orientation with respect to the magnetic medical device 100.

The external magnetic field required to manipulate the catheter is comparable to that used in "conventional" magnetic guidance, since in both cases, the catheter magnetic moment is comprised of a strong permanent magnet.

Figure 12:
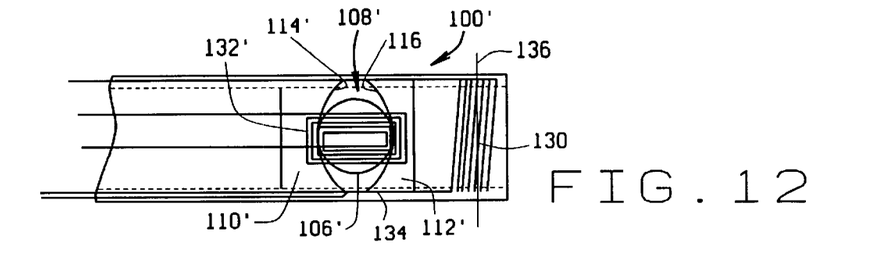
FIG. 12 is a top plan view of the distal end of a magnetic medical device constructed according to a second construction of the second embodiment of this invention.
Figure 13:
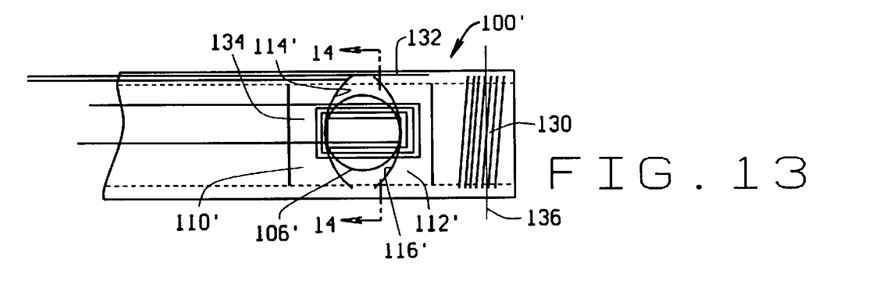
FIG. 13 is a side elevation view of the distal end of the magnetic medical device of the second construction of the second embodiment.
Figure 14:
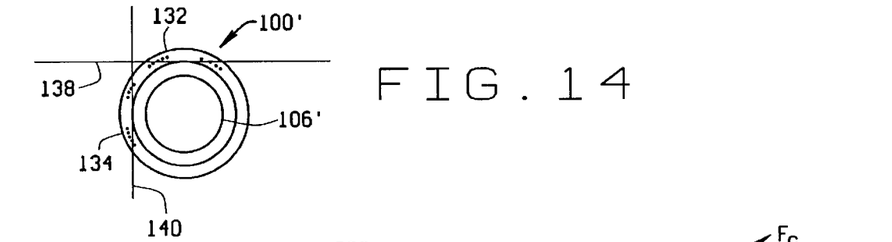
FIG. 14 is a transverse cross-sectional view of the magnetic medical device of the second construction of the second embodiment, taken along the plane of line 9—9 in FIG. 8.
Figure 15A:
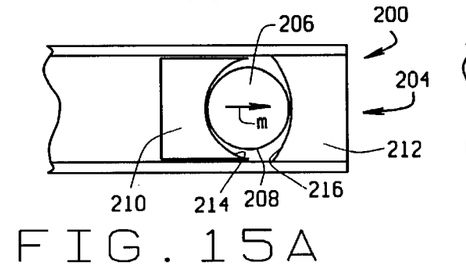
FIG. 15A is a longitudinal cross-sectional view of the distal end of a magnetic medical device according to a third embodiment of this invention, showing the permanent magnet locked in a first position.
Figure 15B:
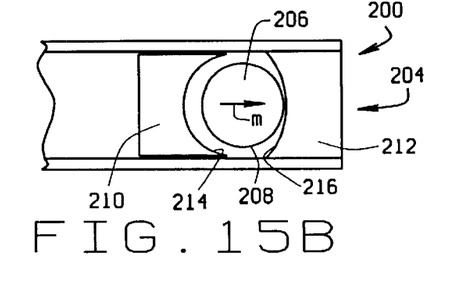
FIG. 15B is a longitudinal cross-sectional view of the distal end of the magnetic medical device of the third embodiment, showing the permanent magnet unlocked in the first position.
Figure 15C:
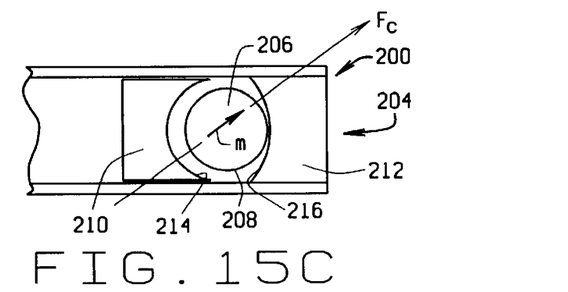
FIG. 15C is a longitudinal cross-sectional view of the distal end of the magnetic medical device of the third embodiment, showing the permanent magnet unlocked in a second position.
Figure 15D:
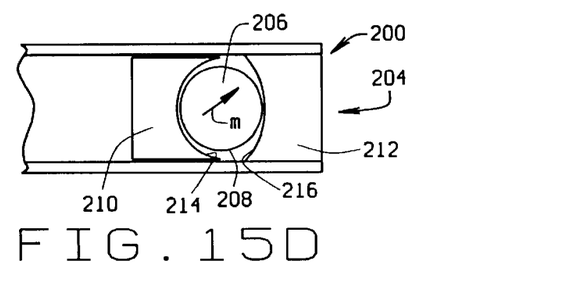
FIG. 15D is a longitudinal cross-sectional view of the distal end of the magnetic medical device of the embodiment, showing the permanent magnet locked in the second position.

An alternate construction of the medical device 100 is indicated generally as 100' in FIGS. 12, 13, and 14. Like medical device 100, the medical device 100' has a magnet body 106 in its distal end portion. This magnet body is trapped in a cage 108' formed by supports 110' proximal to the magnet body, and 112' distal to the magnet body. The cage 108' allows the magnet body to rotate, but substantially restricts axial or radial movements. The distal face 114' of the support 110' is smoothly, concavely curved and the proximal face 116' of the support 112' is likewise smoothly concavely, curved to restrict the axial and radial movement of the magnet body, while otherwise permitting it to turn. The magnet body 106' preferably has a smooth curved surface to facilitate its movement on the faces 114' and 116'. As shown in the figures the magnet body 106 is a sphere, but it could be some other shape, such as an elipsoid.

Magnetic medical device 100', unlike magnetic medical device 100, does not have the two pairs of opposing acutator wires 118, 120 and 122, 124 for controlling the orientation of the magnet body 106. Instead, medical device 100' has coils for generating a local magnetic field for changing the orientation of the magnet body 106. In this alternative construction of the second preferred embodiment there are preferably three coils 130, 132, and 134 which are preferably arranged in three mutually perpendicular planes. The coil 130 is preferably embedded in the wall of the magnetic medical device 100' adjacent the distal end 104 and extends circumferentially around the distal end portion of the magnetic medical device. The coil 130 is generally oriented in a plane 136 transverse to the axis of the magnetic medical device. The coil 132 is also preferably embedded in the wall of the magnetic medical device 100' near the distal end. The coil 132 is generally in a plane 138 parallel to the longitudinal axis of the magnetic medical device 100'. The coil 134 is generally in a plane 140 parallel to the longitudinal axis of the device and perpendicular to the plane 136 in which coil 130 lies.

By selectively applying currents to the coils 130, 132, and 134, magnetic fields of virtually any direction can be applied to the magnet body 106, which tends to align with the local field direction created by the coils. A locking device can be provided to lock the magnet body 106 in its selected orientation, so that the coils 130, 132, and 134 do not have to remain energized to maintain the selected orientation of the magnetic body, only to change the orientation of the magnetic body to the selected orientation.

The coils 130, 132, and 134 can have the same construction and number of turns as discussed above, for coils 26, 28, and 30. With a current of 0.1 amps applied to the coils, each can generate a local magnetic field of about 0.1 T in an orthogonal direction to orient the permanent magnet. If this local field exceeds the strength of the externally applied navigating magnetic field, the magnet will preferably align with the local field, and a torque will be applied to the tip of the magnetic medical device 100' to bring the magnetic moment of the magnet body 106 into alignment with the external magnetic field. The magnetic moment of a permanent magnet, such as magnet body 106, is about ten times larger than the moment of the local coils 130, 132, and 134, so the orientation of the magnet moment of the magnet body 106 will determine catheter alignment in the externally applied navigating magnetic field. If the local field is much less than the externally applied navigating magnetic field, then the magnetic moment of the magnet body 106 will align with the externally applied navigating magnetic field, independent of the coil currents, and navigation using the coils will not be possible. In this case, the external field can be reduced to a value smaller than the local fields to allow the magnetic moment of the magnet body 106 to align with the local field. The magnet body 106 can then be locked in place while the external field is ramped up to its desired value. Once the magnet body 106 is locked in place, the currents in the local coils 130, 132, and 134 can be reduced to zero.

A third embodiment of a magnetic medical device constructed according to the principles of this invention is indicated generally as 200 in FIGS. 15A, 15B, 15C, and 15D. As indicated above, the magnetic medical device may be any device that a physician might want to navigate through the body, such as a catheter, an electrode, a biopsy tool or an endoscope. The device 200 typically has a proximal end (not shown) and a distal end 204. There is a magnet body 206 inside the distal end portion of the magnetic medical device 200. The magnet body 206 is preferably made from a strong permanent magnetic material, such as neodymium-iron-boron, or other suitable material. The magnet body 206 is trapped within a cage 208 formed by a movable support 210 proximal to the magnet body, and a fixed support 212 distal to the magnet body. The cage 208 allows the magnet body to rotate, but substantially limits axial or radial movements. The distal face 214 of the support 210 is smoothly, concavely curved and the proximal face 216 of the support 212 is likewise smoothly concavely, curved to restrict the axial and radial movement of the magnet body, while otherwise permitting it to turn. The magnet body 206 preferably has a smooth curved surface to facilitate its movement on the faces 214 and 216. As shown in the figures the magnet body 206 is a sphere, but it could be some other shape, such as an elipsoid.

The moveable support 210 can be moved axially proximally away from the magnet body 206 to an unlocked position and distally toward the magnet body 206 to a locked position in which it pins the magnet body 206 against the fixed support 212 to lock the magnet body against movement relative to the device 200. When the moveable support 210 is moved to its unlocked position proximally away from the magnet body 206 the magnet body can freely move into alignment with an externally applied magnetic field, and when the moveable support 210 is moved to its locked position, pinning the magnet body 206 against the support 212, the orientation of the magnet body 206 is locked relative to the device 200, and will not change even if the externally applied magnetic field is changed.

Alternate locking mechanisms are possible, such as a microballoon, which is inflated against magnetic 206 to prevent movement Operation In operation, the magnetic medical device 20 of the first embodiment is introduced into the operating region of the patient's body. A relatively strong magnetic field (between about 0.5 T and about 5 T), of substantially uniform direction (at least within the operating region) is applied to the operating region, preferably with an external source magnet. The external source magnet can be one or more permanent magnets, electromagnets, or superconducting electromagnets. The coils 26, 28, and 30 can be selectively energized to create a selected local magnetic moment in the distal end portion of the device 20, which responds to the externally applied magnetic field, causing the distal end portion of the device 20 to move relative to the applied magnetic field. Once in its desired orientation, the distal end 24 of the magnetic medical device 20 can be advanced. When a further change of direction is desired, the currents to the coils 26, 28, and 30 are changed to appropriate values to change the direction of the magnetic moment of the magnetic medical device to cause the distal end portion of the magnetic medical device to move to the desired orientation in the externally applied magnetic field. Through this method of successive orientation of the distal end 24 of the magnetic medical device 20, and advancement of the magnetic medical device in the selected direction, the distal end of the magnetic medical device can be navigated anywhere in the body, and particularly through body lumens and cavities.

To avoid excessive heating of the coils, the coils are preferably only energized when actively redirecting the magnetic medical device. Alternatively, or in addition, the coils can be energized with a pulsed current. The medical device will have a characteristic recovery time, in which the distal end portion of the device "recovers" from being bent. By pulsing the currents in the coils at time intervals shorter than this recovery time, the magnetic medical device can be maintained in an orientation without the constant application of current to the coils. For example, in catheters under 3 mm in diameter made of polymeric materials, typical recovery times for the catheter to straighten from a bend can be measured in seconds. By pulsing the current more frequently, the orientation of the catheter can generally be maintained.

In operation, the magnetic medical device 100 of the first construction of the second embodiment is introduced into the operating region of the patient's body. A magnetic field (between about 0.05 and about 0.5 T), of substantially uniform direction (at least within the operating region) is applied to the operating region, preferably with an external source magnet. The external source magnet can be one or more permanent magnets, electromagnets, or superconducting electromagnets. The magnet body 106 can be selectively oriented to change the local magnetic moment in the distal end portion of the device 100 by pulling or pushing on the actuator wire pairs 118, 120 and 122, 124, to move the magnet body 106 within the cage 108. An optional locking device can be used to lock the magnet body 106 in its selected orientation. The magnet moment of the magnetic medical device 100 responds to the externally applied magnetic field, causing the distal end portion of the device 100 to move relative to the field. Once in its desired orientation, the distal end 102 of the magnetic medical device 100 can be advanced. When a further change of direction is desired, the actuator wire pairs 118, 120 and 122, 124 are again used to changed the orientation of the magnet body 106 to change the direction of the magnetic moment of the magnetic medical device 100 to cause the distal end portion of the magnetic medical device to move to the desired orientation in the externally applied magnetic field. Through this method of successive orientation of the distal end of the magnetic medical device 100, and advancement of the magnetic medical device in the selected direction, the distal end of the magnetic medical device can be navigated anywhere in the body, and particularly through body lumens and cavities.

While the actuator wires 118, 120 and 122, 124 will usually be able to provide sufficient force to reorient the magnet body 106 within the magnetic field applied by the external source magnet, in some instances it may be desirable to remove the external source field while the actuator wires 118, 120 and 122, 124 are being used to reorient the magnetic body 106, and to reapply the external source field after the magnet body has been moved to its selected orientation.

In operation, the magnetic medical device 100' of the second construction of the second embodiment is introduced into the operating region of the patient's body. A relatively strong magnetic field (between about 0.05 T and about 0.5 T), of substantially uniform direction (at least within the operating region) is applied to the operating region, preferably with an external source magnet. The external source magnet can be one or more permanent magnets, electromagnets, or superconducting electromagnets. The coils 126, 128, and 130 can be selectively energized to create a selected local magnetic field in the distal end portion of the device 20, to orient the magnet body 106 in the direction of the field. Once the magnet body 106 is in its desired orientation with respect to the magnetic medical device 100', it can optionally be locked in that position, for example by moving the proximal support 110 distally to pin the magnet body against the distal support 112, or by pulling the distal support proximally, to pin the magnet body against the proximal support. Once the magnet body 106 is locked in its desired orientation, then the coils 126, 128, and 130 can be deenergized, preventing excessive heating of the coils. The magnetic moment in the distal end of the magnetic medical device 100' responds to the externally applied magnetic field, causing the distal end portion of the device 100' to move relative to the field. Once in its desired orientation the distal end of the magnetic medical device 100' can be advanced. When a further change of direction is desired, the currents to the coils 126, 128, and 130 are changed to appropriate values to change the orientation of the magnet body 106 to change the direction of the magnetic moment of the magnetic medical device 100' to cause the distal end portion of the magnetic medical device to move to the desired orientation in the externally applied magnetic field. The magnet body 106 is then unlocked so that it moves to its desired orientation relative to the magnetic medical device 100', thereby causing the magnetic medical device to move to its desired orientation relative to the applied magnetic field. Through this method of successive orientation of the distal end of the magnetic medical device 100', and advancement of the magnetic medical device in the selected direction, the distal end of the magnetic medical device can be navigated anywhere in the body, and particularly through body lumens and cavities.

By locking the magnet body 106, the coils 126, 128, and 130 only have to remain on while the magnet body is being repositioned, and this reduces the risk of overheating. While the coils 126, 128, and 130 will usually be able to generate a local field sufficient to reorient the magnet body 106 within the magnetic field applied by the external source magnet, in some instances it may be desirable to remove the external source field while the coils 126, 128,and 130 are reorienting the magnetic body, and to reapply the external source field after the magnet body 106 has been moved to its selected orientation.

In operation, the magnetic medical device 200 of the third embodiment is introduced into the operating region of the patient's body. The locking mechanism is unlocked by moving the support 210 from its locked position (FIG. 15A) to its unlocked position (FIG. 15B) to allow the magnet body 206 to move freely in the distal end. The support can be operated with a mechanical device such as a push wire (not shown), by fluid pressure, or any other suitable means. A configuring magnetic field $F_C$ (between about 0.0005 and about 0.005 T), of substantially uniform direction (at least within the operating region) is applied to the operating region, preferably with external source magnets. See FIG. 15C. The external source magnet can be one or more permanent magnets, electromagnets, or superconducting electromagnets. This field $F_C$ causes the magnet moment m of the magnet body 206 to align with it, thereby moving the magnet body to the desired orientation relative to the distal end of the device 200 for the planned subsequent navigation. The magnet body 206 is then locked in its orientation by advancing the support 210. See FIG. 15D. A relatively strong navigation magnetic field (between about 0.05 T and about 0.5 T), of substantially uniform direction (at within the operating region) is then applied to the operating region, preferably with the same external source magnet used to apply the configuring magnetic field. The external source magnet can be one or more permanent magnets, electromagnets, or superconducting electromagnets. The magnetic moment in the distal end of the magnetic medical device 200 generated by the magnet body 206 responds to the externally applied magnetic field, causing the distal end portion of the device 200 to move relative to the field. Once in its desired orientation the distal end 204 of the magnetic medical device 200 can be advanced. When a further change of direction is desired, the applied navigating field can be removed, and the magnet body 206 unlocked. A configuring field can then be applied in appropriate direction to achieve the desired new orientation, and the magnet body 206 again locked. The configuring field is removed, and the navigating field reestablished to cause the distal end 204 of the magnetic medical device 200 to move to the desired orientation in the externally applied magnetic field. Through this method of successive orientation of the distal end of the magnetic medical device 200, and advancement of the magnetic medical device in the selected direction, the distal end of the magnetic medical device can be navigated anywhere in the body, and particularly through body lumens and cavities.

This magnetic medical device can also be used with a variable externally applied navigating magnetic field. However, the ability to reorient the magnetic moment of the magnetic medical device, allows greater freedom of navigation, for example where further changes to the navigating magnetic field are difficult or precluded, as might happen where the magnet were close to the patient and could not be moved further, the magnetic moment in the medical device can be changed so that a different navigating magnetic field, that the external source magnet can generate, can be used.

What is claimed is:

1. A method of navigating a medical device having a changeable magnetic moment within an operating region within a patient, the method comprising;
    applying a navigating magnetic field to the operating region with an external source magnet;
    changing the direction of the magnetic moment in the medical device to change the orientation of the medical device in a selected direction within the operating region; and varying the direction of the navigating field applied to the operating region to change the orientation of the medical device.

2. A method of navigating a medical device having a changeable magnetic moment within an operating region within a patient, the medical device including a moveable permanent magnet, the method comprising;
    applying a navigating magnetic field to the operating region with an external source magnet;
    changing the direction of the magnetic moment in the medical device to change the orientation of the medical device in a selected direction within the operating region, the step of changing the direction of the magnetic moment in the medical device comprising moving the permanent magnet relative to the medical device.

3. A method of navigating a medical device having a changeable magnetic moment within an operating region within a patient, the medical device comprising a moveable permanent magnet, moveable relative to the medical device, and a lock for locking the permanent magnet against movement relative to the medical device; the method comprising:
    applying a navigating magnetic field to the operating region with an external source magnet;
    changing the direction of the magnetic moment in the medical device to change the orientation of the medical device in a selected direction within the operating region, the step of changing the direction of the magnetic moment in the medical device comprising disengaging the lock to release the magnet; moving the permanent magnet, and engaging the lock to secure the permanent magnet against movement relative to the medical device.

4. The method according to claim 3 further comprising the step of varying the direction of the navigating magnetic field applied to the operating region to change the orientation of the medical device.

5. A method of navigating a medical device having a changeable magnetic moment within an operating region within a patient, the medical device comprising a moveable permanent magnet, and a mechanism for moving the permanent magnet relative to the medical device, the method comprising:
    applying a navigating magnetic field to the operating region with an external source magnet;
    changing the direction of the magnetic moment in the medical device to change the orientation of the medical device in a selected direction within the operating region, the step of changing the direction of the magnetic moment in the medical device comprising operating the mechanism to move the permanent magnet relative to the medical device.

6. A method of navigating a medical device having a changeable magnetic moment within an operating region within a patient, wherein the medical device comprises a moveable permanent magnet, a mechanism for moving the permanent magnet relative to the medical device, and a lock for locking the permanent magnet against movement relative to the medical device, the method comprising;
    applying a navigating magnetic field to the operating region with an external source magnet;
    changing the direction of the magnetic moment in the medical device to change the orientation of the medical device in a selected direction within the operating region, the step of changing the direction of the magnetic moment in the medical device comprising disengaging the lock to release the magnet, operating the mechanism to move the permanent magnet relative to the medical device; and engaging the lock to secure the permanent magnet.

7. A method of navigating a medical device having a changeable magnetic moment within an operating region within a patient, the medical device comprising a moveable permanent magnet and a lock for locking the permanent magnet against movement relative to the medical device, the method comprising;
    applying a navigating magnetic field to the operating region with an external source magnet;
    changing the direction of the magnetic moment in the medical device to change the orientation of the medical device in a selected direction within the operating region, the step of changing the direction of the magnetic moment in the medical device comprising applying an aligning magnetic field to the operating region in a first direction to align the permanent magnet to provide the desired magnetic moment direction, and engaging the lock to secure the permanent magnet.

8. The method according to claim 7 further comprising applying a navigating magnetic field in a second direction to cause the magnetic medical device to orient in a desired direction.

9. A method of navigating a medical device having a changeable magnetic moment within an operating region within a patient, the medical device comprising a moveable permanent magnet, and at least one electromagnetic coil for applying a magnetic field to move the permanent magnet, the method comprising;
    applying a navigating magnetic field to the operating region with an external source magnet;

changing the direction of the magnetic moment in the medical device to change the orientation of the medical device in a selected direction within the operating region the step of changing the direction of the magnetic moment in the medical device comprising applying an electric current to at least one electromagnetic coil to move the permanent magnet in a desired direction relative to the medical device.

10. The method according to claim 9 wherein the medical device further comprises a lock for locking the permanent magnet against movement relative to the medical device, and wherein the step of changing the direction of the magnetic moment in the medical device further comprises the steps of unlocking the permanent magnet; applying an electric current to the at least one electromagnet coil to move the permanent magnet in the desired direction relative to the medical device; and engaging the lock to lock the permanent magnet against movement relative to the medical device.

11. The method according to claim 9 wherein the medical device further comprises a lock for locking the permanent magnet against movement relative to the medical device, and wherein the step of changing the direction of the magnetic moment in the medical device further comprises the steps of reducing the navigating magnetic field; unlocking the permanent magnet; applying an electric current to the at least one electromagnet coil to move the permanent magnet in the desired direction relative to the medical device; and engaging the lock to lock the permanent magnet against movement relative to the medical device.

12. A method of navigating a medical device within an operating region in the body of a patient, the medical device having at least one coil therein, the method comprising:
    establishing a navigating magnetic field in the operating region;
    selectively energizing the at least one coil in the medical device to create a magnetic moment in the medical device and creating a torque tending to align the magnetic moment of the magnetic medical device with the applied magnetic field; and varying the direction and/or intensity of the applied magnetic field to orient the medical device.

13. The method according to claim 12 wherein the navigating magnetic field in the operating region is established with a source magnet outside of the patient's body.

14. The method according to claim 13 wherein the source magnet comprises at least one electromagnet.

15. The method according to claim 13 wherein the source magnet comprises at least one permanent magnet.

16. A method of navigating a medical device within an operating region in the body of a patient, the medical device having at least one coil therein, the method comprising:
    establishing a navigating magnetic field in the operating region;
    selectively energizing the at least one coil in the medical device to create a magnetic moment in the medical device and creating a torque tending to align the magnetic moment of the magnetic medical device with the applied magnetic field, the step of selectively energizing the at least one coil comprises applying electrical energy in pulses to the at least one coil in the medical device.

17. The method according to claim 16 wherein the medical device is flexible and has a characteristic recovery time in which the device recovers from being flexed, and wherein the time between pulses is less than the characteristic recovery time of the medical device.

18. A method of navigating an elongate medical device within an operating region in the body of a patient, the medical device having a proximal end, a distal end, and at least one coil adjacent the distal end, the method comprising:
    introducing the distal end of the medical device into the operating region in the patient's body;
    establishing a navigating magnetic field in the operating region;
    selectively energizing the at least one coil adjacent the distal end of the elongate medical device to create a magnetic moment at the distal end of the elongate medical device to turn the distal end of the elongate medical device in the desired direction; and varying the direction and/or intensity of the applied magnetic field to orient the elongate medical device.

19. The method according to claim 18 wherein the navigating magnetic field in the operating region is established with a source magnet outside the patient's body.

20. The method according to claim 19 wherein the source magnet comprises at least one electromagnet.

21. The method according to claim 19 wherein the source magnet comprises at least one permanent magnet.

22. A method of navigating an elongate medical device within an operating region in the body of a patient, the medical device having a proximal end, a distal end, and at least one coil adjacent the distal end, the method comprising:
    introducing the distal end of the medical device into the operating region in the patient's body;
    establishing a navigating magnetic field in the operating region;
    selectively energizing the at least one coil adjacent the distal end of the elongate medical device to create a magnetic moment at the distal end of the elongate medical device to turn the distal end of the elongate medical device in the desired direction, the step of selectively energizing the least one coil comprising applying electrical energy in pulses to the at least one coil in the medical device.

23. The method according to claim 22 wherein the elongate medical device is flexible, and has a characteristic recovery time in which the device returns to its normal configuration from a deflected configuration, and wherein the at least one coil is energized at a pulse rate faster than the characteristic recovery time of the elongate medical device.

24. A method of navigating an elongate medical device within an operating region in the body of a patient, the medical device having a proximal end, a distal end, and at least one coil adjacent the distal end, the method comprising:
    introducing the distal end of the medical device into the operating region in the patient's body;
    establishing a navigating magnetic field in the operating region;
    selectively energizing the at least one coil adjacent the distal end of the elongate medical device to create a magnetic moment at the distal end of the elongate medical device to turn the distal end of the elongate medical device in the desired direction, by applying electrical energy in pulses to the at least one coil in the medical device to retain the coils below a temperature that is harmful to tissue.

25. A method of navigating an elongate medical device within an operating region in the body of a patient, the medical device having a proximal end, a distal end, and at least one coil adjacent the distal end, the method comprising:
    introducing the distal end of the medical device into the operating region in the patient's body;
    establishing a navigating magnetic field in the operating region;

selectively energizing the at least one coil adjacent the distal end of the elongate medical device to create a magnetic moment at the distal end of the elongate medical device to turn the distal end of the elongate medical device in the desired direction, by applying electrical energy in pulses to the at least one coil in the medical device to retain a temperature below about 45° C.

26. A method of navigating an elongate medical device within an operating region in the body of a patient, the medical device having a proximal end, a distal end, and at least one coil adjacent the distal end, the method comprising:

introducing the distal end of the medical device into the operating region in the patient's body;

establishing a navigating magnetic field in the operating region;

selectively energizing the at least one coil adjacent the distal end of the elongate medical device to create a magnetic moment at the distal end of the elongate medical device to turn the distal end of the elongate medical device in the desired direction, by applying electrical energy in pulses to the at least one coil in the medical device to retain a balance between the heat generated in the coil and the heat conducted from the coil by the flow of body fluids past the coils.

27. An elongate medical device having a proximal end and a distal end, the distal end adapted to be navigated within the body with an externally applied magnetic field, the medical device comprising a permanent magnet body in the distal end of the medical device, the magnetic body being moveable to change the direction of the magnetic moment of the magnetic body relative to the medical device.

28. The elongate medical device according to claim 27 further comprising a mechanism for selectively moving the permanent magnet in the medical device to change the direction of the magnetic moment relative to the medical device.

29. The elongate medical device according to claim 28 further comprising a lock for selectively locking the permanent magnet body against movement relative to the magnetic medical device.

30. The elongate medical device according to claim 27 wherein the mechanism for selectively moving the permanent magnet includes pull wires extending of the proximal end of the device for manipulating the permanent magnet.

31. The elongate medical device according to claim 30 further comprising a lock for selectively locking the permanent magnet body against movement relative to the magnetic medical device.

32. The elongate medical device according to claim 27 further comprising at least one electromagnetic coil, which when energized, can move the permanent magnet body.

33. The elongate medical device according to claim 32 further comprising a lock for selectively locking the permanent magnet body against movement relative to the magnetic medical device.

34. The elongate medical device according to claim 32 wherein there are at least two electromagnetic coils in the distal end of the medical device.

35. The elongate medical device according to claim 32 wherein there are at least three electromagnetic coils in the distal end of the medical device.

* * * * *